(12) United States Patent
Woodyear

(10) Patent No.: US 10,896,752 B2
(45) Date of Patent: Jan. 19, 2021

(54) SYSTEM AND METHOD FOR THE VERIFICATION OF MEDICATION

(71) Applicant: John Woodyear, Troy, NC (US)

(72) Inventor: John Woodyear, Troy, NC (US)

(*) Notice: Subject to any disclaimer, the term of this patent is extended or adjusted under 35 U.S.C. 154(b) by 0 days.

(21) Appl. No.: 16/233,173

(22) Filed: Dec. 27, 2018

(65) Prior Publication Data

US 2019/0139639 A1 May 9, 2019

Related U.S. Application Data

(63) Continuation-in-part of application No. 15/420,768, filed on Jan. 31, 2017.

(60) Provisional application No. 62/294,044, filed on Feb. 11, 2016.

(51) Int. Cl.
*G16H 20/13* (2018.01)
*G06K 9/00* (2006.01)
*A61J 7/00* (2006.01)
*A61J 7/04* (2006.01)
*G16H 20/10* (2018.01)
*A61J 1/06* (2006.01)

(52) U.S. Cl.
CPC .............. *G16H 20/13* (2018.01); *A61J 1/065* (2013.01); *A61J 7/0076* (2013.01); *A61J 7/0481* (2013.01); *G06K 9/00288* (2013.01); *G16H 20/10* (2018.01); *A61J 2200/30* (2013.01); *A61J 2200/70* (2013.01); *A61J 2205/10* (2013.01); *A61J 2205/20* (2013.01); *A61J 2205/30* (2013.01)

(58) Field of Classification Search
CPC ....... G16H 20/13; G16H 10/60; A61J 7/0481; A61J 7/0069; A61J 7/0418; A61J 7/0427; A61J 7/049; G06K 9/00255
USPC .......................................................... 705/2
See application file for complete search history.

(56) References Cited

U.S. PATENT DOCUMENTS

| | | | |
|---|---|---|---|
| 5,700,998 | A | 12/1997 | Palti |
| 5,845,264 | A | 12/1998 | Nellhaus |
| 7,630,908 | B1 | 12/2009 | Amrien et al. |
| 7,793,836 | B2 | 9/2010 | Radatti et al. |
| 8,626,672 | B2 | 1/2014 | Stuck et al. |
| 2006/0265134 | A1 | 11/2006 | Radatti et al. |
| 2007/0047770 | A1* | 3/2007 | Swope ............. A61B 5/1171 382/115 |
| 2007/0265880 | A1 | 11/2007 | Bartfeld et al. |
| 2008/0120698 | A1 | 5/2008 | Ramia |
| 2011/0008527 | A1 | 1/2011 | Teggatz et al. |

(Continued)

FOREIGN PATENT DOCUMENTS

| | | |
|---|---|---|
| CA | 2327283 A1 | 10/1999 |
| WO | 2013139221 A1 | 9/2013 |

*Primary Examiner* — Hiep V Nguyen
(74) *Attorney, Agent, or Firm* — King & Wood Mallesons LLP

(57) ABSTRACT

A system and method for verifying proper possession of a medication is disclosed. A reader device scans a code printed on the medication to extract an embedded serial number and captures an image of the face of the person in possession of the medication. A first server queries a prescription database, which retrieves facial characteristic data associated with the embedded serial number. A determination is made if the retrieved facial characteristic data matches facial characteristic data extracted from the captured image. The match information is displayed on the reader device.

16 Claims, 10 Drawing Sheets

(56) References Cited

U.S. PATENT DOCUMENTS

| | | |
|---|---|---|
| 2011/0015945 A1 | 1/2011 | Addy |
| 2011/0100863 A1 | 5/2011 | Luciano |
| 2012/0183941 A1 | 7/2012 | Steinmetz |
| 2012/0185267 A1* | 7/2012 | Kamen ................. G06Q 50/22 |
| | | 705/2 |
| 2013/0026226 A1 | 1/2013 | Luciano, Jr. et al. |
| 2014/0067426 A1 | 3/2014 | Neff |
| 2014/0089011 A1* | 3/2014 | Fletcher ................. G06Q 50/22 |
| | | 705/3 |
| 2014/0149131 A1 | 5/2014 | Bear et al. |
| 2015/0100343 A1* | 4/2015 | Siedlecki ............ G06F 19/3456 |
| | | 705/2 |

* cited by examiner

SYSTEM AND METHOD FOR THE VERIFICATION OF MEDICATION

CROSS-REFERENCE TO RELATED APPLICATION

This application is a continuation in part of U.S. application Ser. No. 15/420,768 filed Jan. 31, 2017, which claims the benefit of U.S. Provisional Patent Application Ser. No. 62/294,044 filed Feb. 11, 2016, the disclosures of all of which are hereby incorporated by reference as if restated in their entireties.

TECHNICAL FIELD

Exemplary embodiments of the present invention relate generally to systems and methods for verifying legitimate possession of a prescription medication.

BACKGROUND AND SUMMARY OF THE INVENTION

The present invention helps alleviate the abuse of prescription drugs by providing a system and method for verifying individual pills by scanning a code printed on said pills, retrieving associated information about the person legally prescribed the pills in question (e.g., their name), and comparing that information to information about the person actually possessing the pill (e.g., against their government issued ID). Drugs, particularly medicines, have the power to treat illnesses and prevent disease when used properly. Drugs also have the power to be abused, cause addiction, and damage the human body when used improperly. In light of this, governments have implemented methods to control the distribution and use of drugs most likely to be abused. Generally speaking, controls appear in the form of prescription requirements wherein a person must be prescribed a set amount of the drug by a licensed medical professional in order to legally possess and use said drug. Unfortunately, control over prescribed pills is lost once they pass over the dispensary's counter. Within the realm of prescription medication controls, drugs most likely to be abused are often further classified and regulated. Typically, a certain number of these drugs are outright banned from being possessed or used (e.g., heroin, cocaine) due to their dangerous nature and relatively low utility in a medical application. Another select group of drugs are permitted to be possessed and used by prescription, but face additional regulations and controls. These often include, without limitation, narcotics, benzodiazepines, sedatives, hypnotics, and central nervous system stimulants.

For example, in the United States, this regulation is achieved in part by the Controlled Substance Act.[1] Under the Controlled Substance Act, these drugs are categorized into "schedules." Each schedule contains a number of types of drugs and has varying degrees of control and regulation. Additionally, most states in the United States have a Prescription Drug Monitoring Program (PDMP), which serves to both protect legitimate users of controlled prescription substances and prevent illegal diversion and use of controlled prescription drugs. Many states have slightly different PDMPs but one feature that is typical of a PDMP or similar program is a state prescription database (e.g., Ohio has OARRS—Ohio Automated Rx Reporting System[2], Indiana has INSPECT[3], etc.). These databases store information regarding the persons to whom controlled substances have been prescribed and information on the controlled substances itself including what was prescribed, when it was prescribed, for how long the treatment is to last, what dosage was prescribed, and the like. This information is used for many purposes including supporting access to legitimate medical use of controlled substances, identifying and deterring or preventing drug abuse and diversion, facilitating and encouraging the identification, intervention with and treatment of persons addicted to prescription drugs, informing public health initiatives through outlining of use and abuse trends, and educating individuals about PDMPs and the use, abuse and diversion of addiction to prescription drugs.[4]

[1] See http://www.fda.gov/regulatoryinformation/legislation/ucm148726.htm; http://www.deadiversion.usdoj.gov/schedules/
[2] https://www.ohiopmp.gov/Portal/Default.aspx
[3] http://www.in.gov/pla/inspect/
[4] http://www.deadiversion.usdoj.gov/faq/rx_monitor.htm Despite these programs and other efforts, control prescription drugs are abused with great frequency. For example, in the United States, 52 million people over the age of 12 have used prescription drugs non-medically in their lifetime. In 2010, there were 8.76 million prescription medicine abuses. Further, only 20% of prescription drugs are obtained from a doctor—54.2% of prescription drugs are obtained free from a friend or relative, 16.6% are bought or taken from a friend or relative, 3.9% are obtained from a drug dealer or a stranger, 0.3% are purchased through the internet, and the rest are unaccounted for.[5] Among the reasons cited by teens to improperly use prescription drugs includes that they are easy to get from parent's medicine cabinets (cited by 62% of those surveyed), they are available everywhere (52%), they are not illegal drugs (51%), they are easy to get through other people's prescriptions (50%), and they can claim to have a prescription if caught (49%).[6]

[5] http://www.drugabuse.gov/related-topics/trends-statistics/infographics/popping-pills-prescription-drug-abuse-in-america
[6] Id.

As the data shows, the current attempts to control prescription drugs are insufficient. One shortfall of the system is that individual pills cannot be verified. For example, if one were to legitimately possess a prescription container for a drug (for the purposes of this example called "Drug X"), the pills in the Drug X container could be substituted with pills containing a controlled substance (for the purposes of this example called "Drug Y"). Upon a cursory review, one may conclude that the person legitimately possesses Drug X, when in reality the person possesses Drug Y in a container intended to carry Drug X. In another example, a person may possess a prescription container for the same controlled substance Drug Y, but be filled with illegally obtained Drug Y pills. Again, upon a cursory review one may conclude that the person legitimately possesses the Drug Y. Stated another way, the user may become addicted to Drug Y during the course of taking a legitimate prescription for Drug Y. The person may keep the Drug Y prescription container and continue to re-fill it with additional, illegally obtained, Drug Y pills. Further still, if a person is found with a legal or illegally possessed drug outside of the prescription container, the pills cannot be individually identified and thus, verification of legitimate possession is not possible. Some of these shortfalls are likely contributors to the continued prescription drug abuse epidemic.

Therefore, what is needed is a system and method for the verification of medication that is capable of individually and securely verifying individual pills. Such a system and method may be used by law enforcement officials to quickly, accurately, and securely identify if a person legally possesses a controlled substance or other prescription medication. The present invention provides such a system and method for the verification of medication that is capable of individually verifying prescription drugs.

The present invention comprises a coding system whereby a medication has been marked with a code, such as a bar code or a quick response (QR) code. The code comprises an embedded serial number that is displayed when the code is read or interpreted by a reader device. The serial number includes a lot or batch number and may include further information such as the identity of the manufacturer. In this way, all medications of a lot or batch may be marked with the same code, which simplifies the marking process such that a unique code need not be printed on each medication. The serial number may be linked to a patient at the time a prescription is filed and be stored in a prescription database.

The present invention further comprises a patient identification system whereby a software application (an "app") or website on a mobile device is designed to read and interpret the code. For example, without limitation, the code may be a QR code that is read by the camera on a smart phone and the information is transmitted to the app for processing. A comparison may then be made to a code printed on the prescription bottle to determine whether a match is made and thus that the pills in the bottle are legitimately possessed by the person.

Alternatively, if a prescription bottle is not present (i.e., the person possesses loose pills), or if the code on the pill does not match the prescription bottle, the code on the pills may be scanned using the app and the person's name may be entered. The app may then relay this information to a first server, which may query the appropriate prescription database. The prescription database may return the name of the person legally prescribed the pills in question. This name may be returned to the device, via the first server, and the device may determine if there is a match between the entered name (the person actually possessing the pills in question) and the returned name (the person legally prescribed the pills in question). In other exemplary embodiments, it may be unnecessary to enter the name of the person actually possessing the pills. In such embodiments, the name of the person legally prescribed the pills may be returned and the user may determine whether the returned name matches the name of the person actually possessing the pills.

In exemplary embodiments, facial recognition technology may be used to identify the person in possession of the pills in question. In such embodiments, the prescription database may comprise facial data for the person legally prescribed the medication. The reader device may be used to scan the code on the medication as well as the face of the person in possession of the medication. This information may be relayed to the appropriate prescription database where a check may be performed and a notification of whether the scanned face is a match or not a match for the person who was legally prescribed the pills may be returned for display on the reader device. The message may be color coded such as green for match and red for no match.

It is contemplated that this system and method may be used in the context of law enforcement to verify the legality of the person's possession of the prescription medication. However, this application is merely exemplary and other applications are contemplated including quality control, preventing drug interactions, and any other application where verification of prescription medication is desirable. Likewise, exemplary users of the present invention include, but are not limited to, law enforcement officials, medical professionals, manufacturers, and anyone else involved in the care, handling, and regulation of prescription drugs.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1:
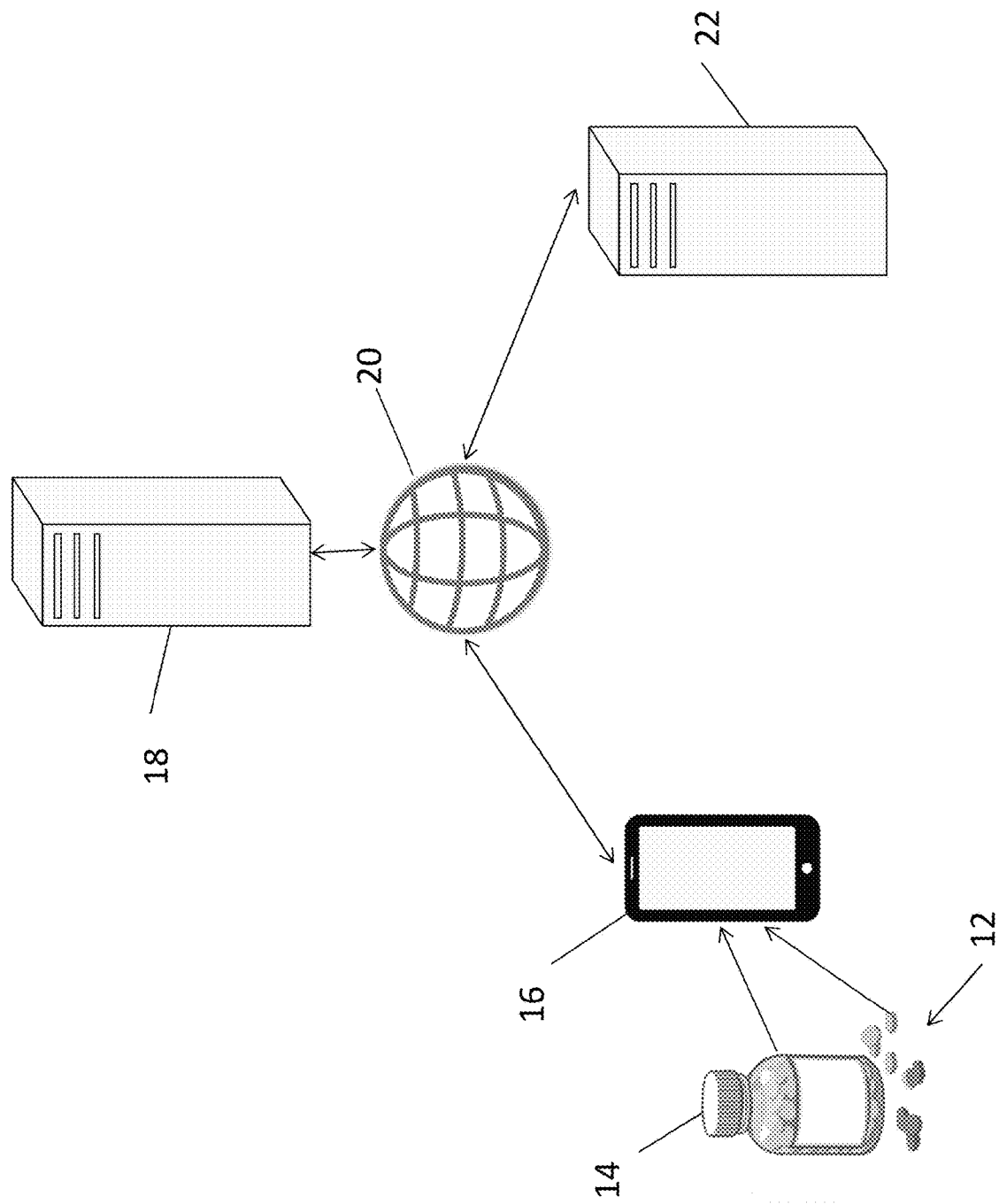
FIG. 1 illustrates an exemplary embodiment of a system in accordance with the present invention.
Figure 2:
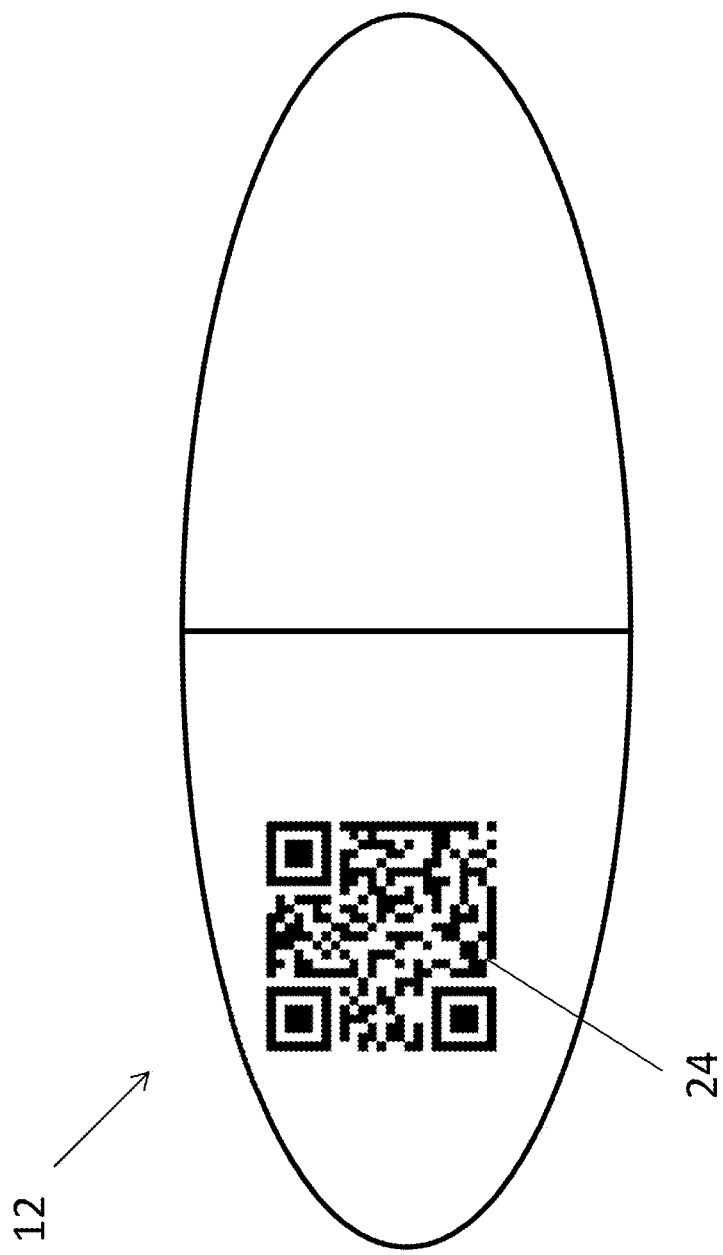
FIG. 2 is a top view of an exemplary pill for use with the system of FIG. 1.
Figure 3:
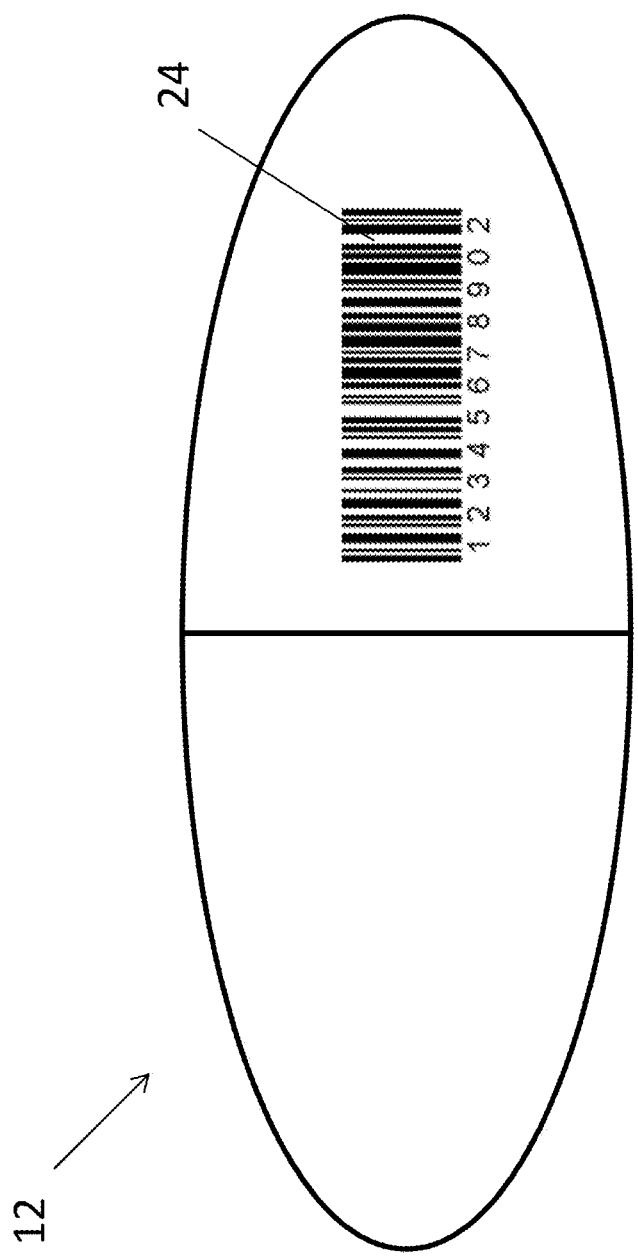
FIG. 3 is a top view of another exemplary pill for use with the system of FIG. 1.

FIG. 1 through FIG. 5 illustrates an exemplary system in accordance with the present invention. A medication 12 such as a pill, tablet, capsule, or the like is marked with a code 24. The code 24 may be a one-dimensional code such as a UPC, EAN, Code 39, Code 128, ITF, Code 93, Codabar, GS1 Databar, MSI Plessey or the like. Alternatively, the code 24 may be a two-dimensional code such as a quick response (hereinafter "OR") code, datamatrix code, PDS417, Aztec, or the like. FIG. 2 and FIG. 3 illustrate detailed views of exemplary medications 12 marked with exemplary codes 24.

Two-dimensional codes are well known in the art. A brief description is provided herein for completeness but is not intended to be limiting. Two dimensional codes are optically machine-readable labels containing encoded information about the item to which it is attached. The QR code, for example without limitation, consists of three alignment targets and a series of black modules (typically square markings) arranged in a square grid on a white background, and are capable of being read by an imaging device such as a camera. Some of the black modules are directed to formatting information and the rest are generally directed to the underlying data, which can be any kind of information. The image is often processed using Reed-Solomon error correction until the image can be appropriately interpreted.

The required data is then extracted from patterns that are present in both horizontal and vertical components of the image and is generally interpreted in numeric, alphanumeric, byte/binary, and Kanji forms, though other forms are possible.

In exemplary embodiments of the present invention, the code 24 comprises encoded data for translating at least a portion of the code 24 into a serial number. The serial may be 10-12 digits, though any number of digits is contemplated, and may comprise letters, numbers, other symbols, or some combination thereof. In other exemplary embodiments of the present invention, the code 24 may be a series of non-encoded letters and/or numbers (i.e., a list of printed letters and/or numbers) of any number of digits. Essentially, in such an embodiment, the code 24 is the serial number. The code 24 or the translated, embedded serial number may comprise a lot or batch number. For example, without limitation, the code 24 may be translated into the serial number, the lot, and batch number. In other exemplary embodiments, at least a portion of the embedded serial number may be the lot and batch number. The code 24 may additionally comprise other embedded information such as, but not limited to, the manufacture date, the manufacture's name or identification information, the content of the medication 12, or any other information about the medication 12 and its manufacture. The serial number may be determined by any known or future standardized system. The serial number may comprise any numbered of coded or uncoded portions that are intended to convey information about the medication 12.

The code 24 may be placed on the medication 12 during manufacture by any known method. Alternatively, the code 24 may be placed on the medication 12 at a later stage. A number of methods and systems for imprinting medication 12 with information are known in the arts. In exemplary embodiments of the present invention, a system and method is used that prints the code 24 with a sufficient resolution that it may be read by a relatively low-resolution camera, such as but not limited to, one on a smart phone or other mobile device. The ink used to print the code 24 may be any ink that is safe for human consumption, such as but not limited to, those approved by the Food and Drug Administration (FDA). The surface of the medication 12 may comprise a coating or surface texture amenable to the adherence of the ink.

The medication 12 having the code 24 printed thereon may then be placed in a storage container 14. The storage container 14 may be any container for storing medication 12. In exemplary embodiments of the present invention, the storage container 14 may be a prescription bottle. In exemplary embodiments of the present invention, only medication 12 from the same lot or batch, such that it contains the same code 24, may be placed in a single storage container 14. Stated another way, medication 12 of a "split lot" or a "split batch" would require separate storage containers 14. This simplifies the printing process, such that a unique code need not be marked on each medication 12.

Figure 4:
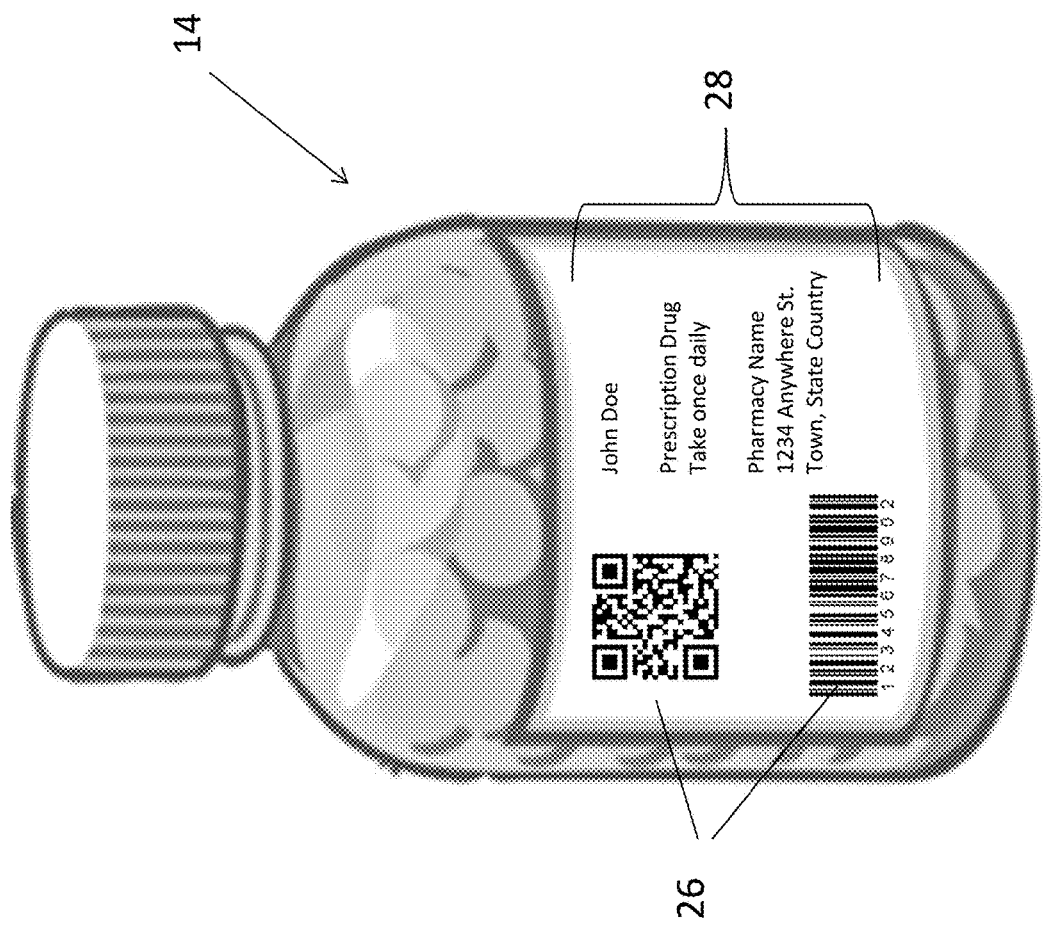
FIG. 4 is a perspective view of an exemplary pill container for use with the system of FIG. 1.
Figure 5:
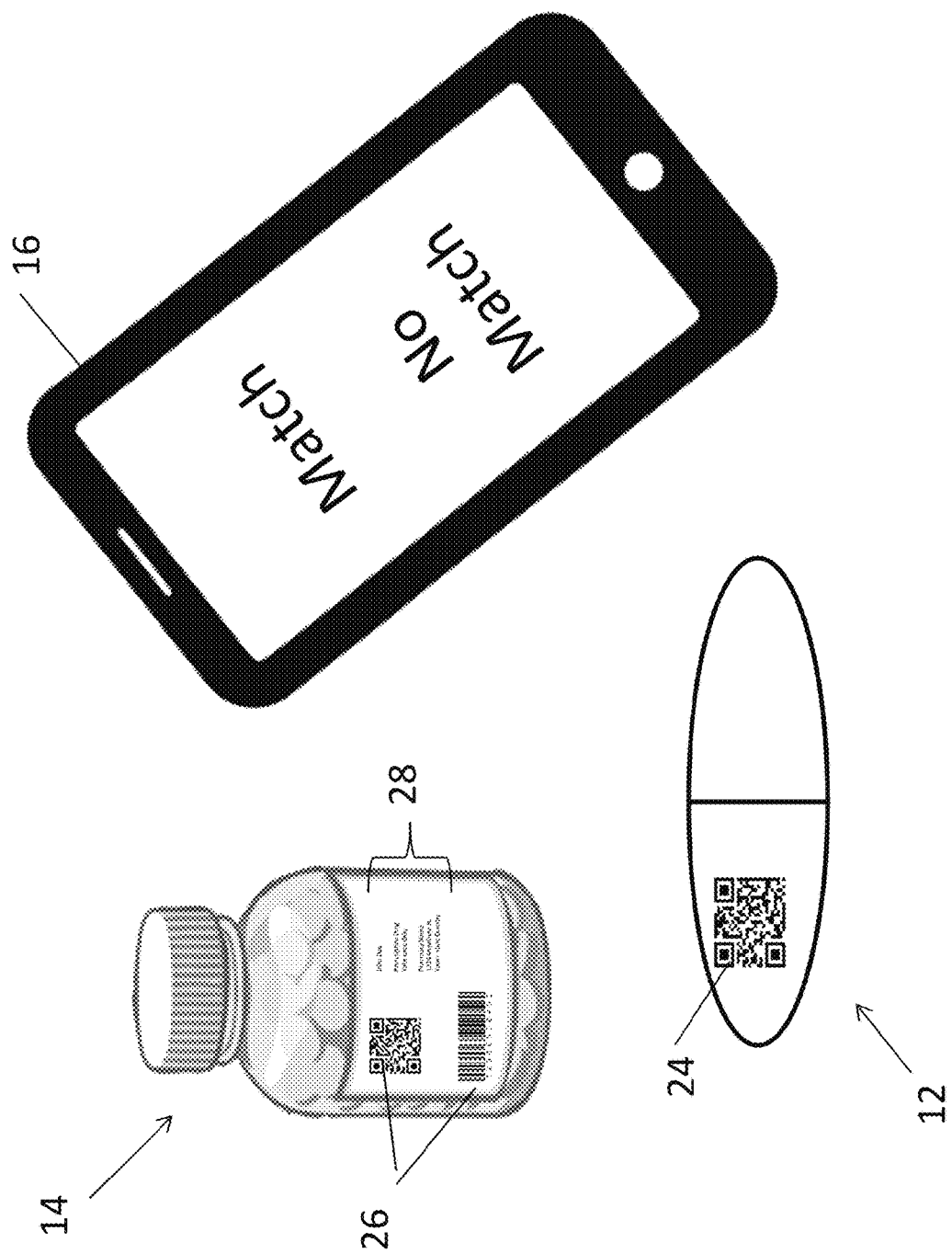
FIG. 5 illustrates a detailed view of the system of FIG. 1.

FIG. 4 illustrates a detailed view of the storage container 14. The storage container 14 may further comprise a label having patient and prescription information 28. In exemplary embodiments of the present invention the storage container 14 further comprises a corresponding code 26. The corresponding code 26, like the code 24, may be a one-dimensional code, a two-dimensional code, or the like. In exemplary embodiments of the present invention the code 24 matches, is identical to, or is otherwise associated with the corresponding code 26. It is notable that the corresponding code 26 is optional and may not be required for exemplary embodiments of the present invention.

The code 24 and the corresponding code 26 may be configured to be read and interpreted by a reader device 16. The reader device 16 may be a mobile device such as a smart phone, camera, tablet, laptop or the like. The reader device 16 may additionally be a dedicated scanning device or attachment for a mobile device, such as a code reading device, a scanner, terminal or any other fixed or mobile device or attachment configured to read and interpret one and two dimensional codes 24. The reader device 16 may be configured to read and interpret the code 24 and the corresponding code 26, input and receive other information, display the encoded information, and input, receive, and display match information. In exemplary embodiments, the encoded information is the serial number comprising at least a lot or batch number and the match information is a message displaying "MATCH" or "NO MATCH" or similar.

As will be explained in greater detail, the system and method described herein may be used by law enforcement officials to determine whether a person carrying medication 12 is legally permitted to possess or use said medication 12. This information may be used to make decisions regarding whether to pursue a further investigation, continue detention of the person, perform a search of the person, their dwelling, vehicle, personal belongings, and the like, or to make an arrest. Alternatively, other applications are contemplated including quality control, preventing drug interactions, and any other application where verification of prescription medication is desirable. Any purpose or application is contemplated.

As best illustrated in FIG. 1, the reader device 16 may be in communication with a first server 18 via a communications network 20, such as the internet. The first server 18 may likewise be in communication with a prescription database 22 via the communications network 20. The prescription database 22 may be part of a state or federally controlled prescription database program, such as but not limited to the PDMP. The prescription database 22 may be a single database or comprise multiple databases that are linked and may be queried together. This may include, but is not limited to, a national network of state prescription databases or a national prescription database.

The first server 18 may receive the serial number and other information from the reader device 16 and send a query to the prescription database 22 to compare the serial number and other information against patient registration information. The query may be an automated request for information from the prescription database 22. As will be described with greater detail herein, the first server 18 may also determine which prescription database 22 to query.

In other exemplary embodiments of the present invention, only the prescription database 22 for the state in which the user is located or employed in may be queried. In still other exemplary embodiments, the prescription database 22 for the state in which the user is located or employed to work in and the adjoining states may be queried. The query of any number of prescription databases 22 for any number of states in any combination is contemplated. The prescription database 22 to be queried may be pre-determined and thus the first server 18 may serve as a relay in communications between the reader device 16 and the prescription database 22.

The prescription database 22 may perform an automated query and determine patient information associated with the serial number. The patient information may include, but is not limited to, the patient's name, address, physical description, prescription information, photograph, and the like. The patient information may then be transmitted back to the first server 18 and back to the reader device 16.

In exemplary embodiments of the present invention, the reader device 16 may also be configured to receive and transmit other input including, but not limited to, the person's name, state where prescription was filled, particular database to be queried, date of birth, and other identifying information. This information may likewise be transmitted via the communications network 20 to the first server 18. The first server 18 may only check to see if the patient information matches the name information transmitted by the reader device 16. The first server 18 may then transmit the match information back to the reader device 16 to be displayed.

In other exemplary embodiments, the name and the serial number information may be transmitted to the prescription database 22 where the prescription database 22 determines whether the information is a match and relays back the match information. In still other exemplary embodiments, the prescription database 22 may transmit corresponding patient information to the first server 18 and the information may be relayed to the reader device 16 and the reader device 16 may determine if there is a match and display the match information. Regardless, the reader device 16 may be configured to display match information to the user including whether or not a match was determined.

In other exemplary embodiments of the present invention, only the serial number may be transmitted to the prescription database 22 and the prescription database 22 may return the patient information associated with the serial number to the reader device 16 such that the user may make a match determination.

In still other exemplary embodiments of the present invention, the reader device 16 may read the code 24 and the corresponding code 26 and display match information. Alternatively, the reader device 16 may read the code 24 and the corresponding code 26 and display the serial numbers for comparison.

Figure 6:
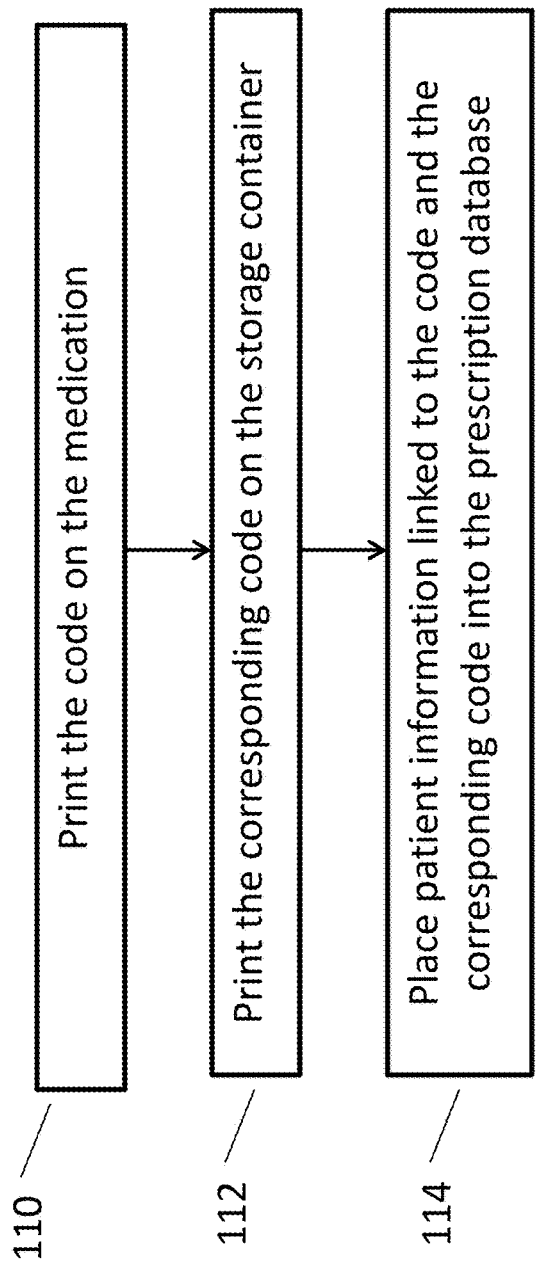
FIG. 6 is an exemplary method in accordance with the present invention.

FIG. 6 illustrates an exemplary method in accordance with the present invention. In step 110 the code 24 may be placed on the medication 12. The code 24 may be placed by printing or any other known method for marking the medication 12. The printing may be accomplished at the manufacturing facility, at the packaging facility, at the dispensing pharmacy, at a separate printing facility, or any other place prior to dispensing the medication 12 to the person. In step 112 the corresponding code 26 is placed on the storage container 14. Likewise, the corresponding code 26 may be placed by printing or any other known method for marking the storage container 14. Finally, in step 114 the code 24 and the corresponding code 26 may be associated with patient information and linked thereto and stored in the prescription database 22.

In exemplary embodiments of the present invention this information may be gathered and linked to or otherwise associated with the patient when the prescription is ordered or filled and may be associated and caused to be placed in the prescription database 22 by the doctor, pharmacist, or other medical professional. The patient information may be manually entered into a computer system. For example, without limitation, this may be done for new patients or when updating patient information. In other exemplary embodiments, the patient information may be automatically entered from information already known by the doctors, pharmacist, or other medical professional. For example, without limitation, this may be done for existing patients by automatically populating a form or uploading information from the medical professional's files. The steps listed are merely exemplary and may be performed in any order. Additionally, various steps may be repeated or omitted.

Figure 7:
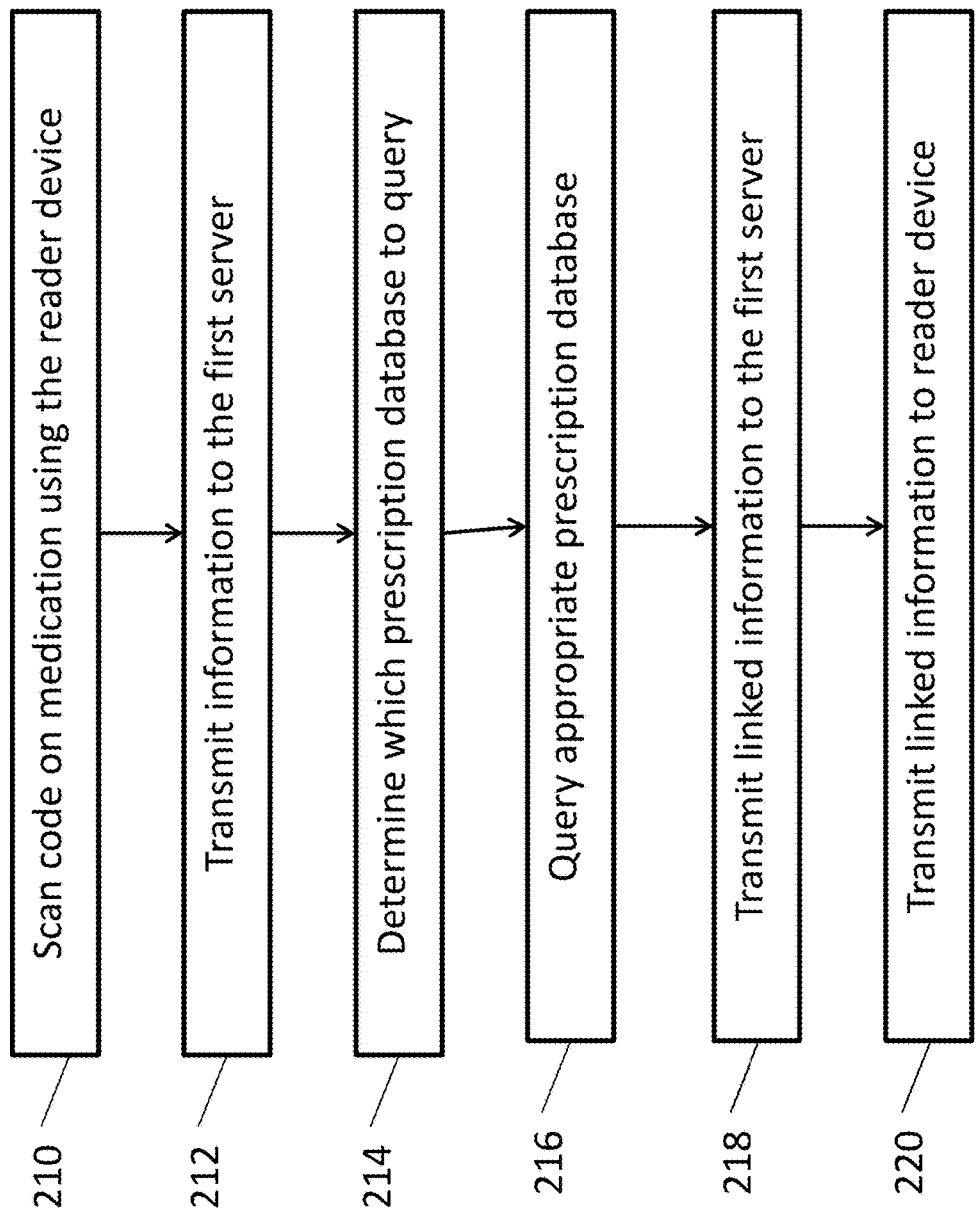
FIG. 7 is another exemplary method.

FIG. 7 illustrates an exemplary method for verifying proper possession of medication. In step 210 the code 24 on the medication 12 may be scanned using the reader device 16. In step 212 the information from the code 24 may be transmitted by the reader device 16 to the first server 18 via the communications network 20. In step 214, the first server 18 may determine which prescription database 22 to query and in step 216 the appropriate prescription database 22 is queried. In exemplary embodiments of the present invention, the prescription database 22 is the state-controlled PDMP, and thus the first server 18 may determine which state's prescription database 22 to query. This may be done by the input from the user and the transmission of additional information from the reader device 16 to the first server 18. This information may include a state selected by the user according to the persons' license information, stated information about the persons' residence, location of prescribing physician, or location of dispensing pharmacy.

In exemplary embodiments of the present invention, the first server 18 may make an assumption on which state databases 22 are to be queried including by first querying the database of the state where the user is located and if no matching information is found, by subsequently querying databases 22 at an increasing geographic distance until matching information is found or all databases 22 have been queried.

Next, in step 218 the corresponding information may be retrieved from the prescription database 22 and transmitted to the first server 18. The first server 18 may then transmit the information to the reader device 16. In step 220, the transmission of information may be accomplished by the communications network 20.

Figure 8:
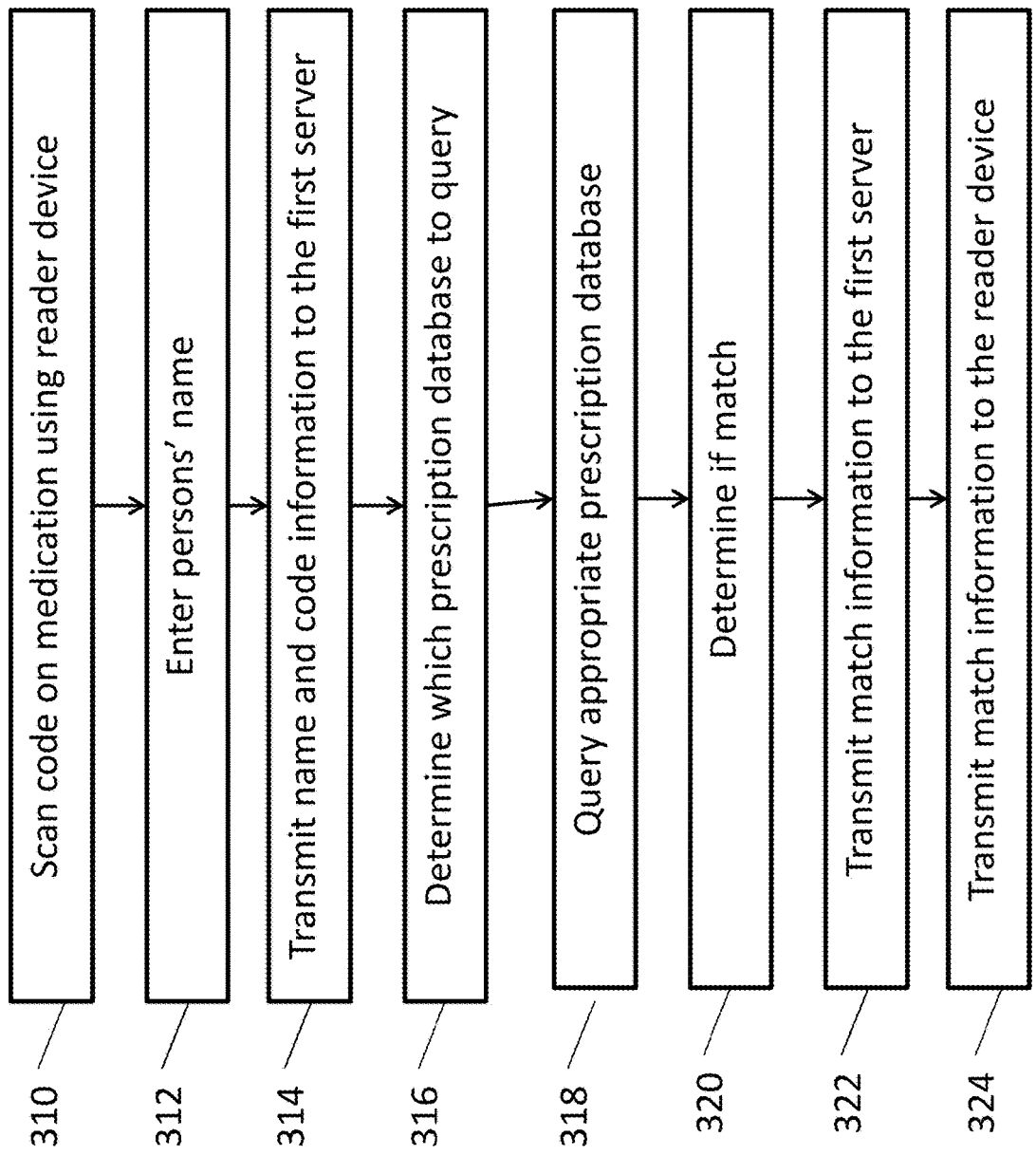
FIG. 8 is another exemplary method.

FIG. 8 illustrates another exemplary method. In step 310 the reader device 16 is used to scan the code 24 on the medication 12. Next, in step 312 the persons' name may be entered into the reader device 16. In step 314 the name and serial number from the code 24 may be transmitted to the first server 18. In step 316 the first server 18 may determine which prescription database 22 to query. Step 316 may be accomplished by any of the several methods previously discussed and in step 318, the appropriate prescription database 22 may be queried. In step 320 the prescription database 22 may determine if there is a match between the name and the code information. The match information may then be transmitted to the first server 18 in step 322. Finally, in step 324, the first server 18 may transmit the match information to the reader device 16. Alternatively, the information may be transmitted from the database and the match determination may be made by the first server 18 or by the user of the reader device 16.

Figure 9:
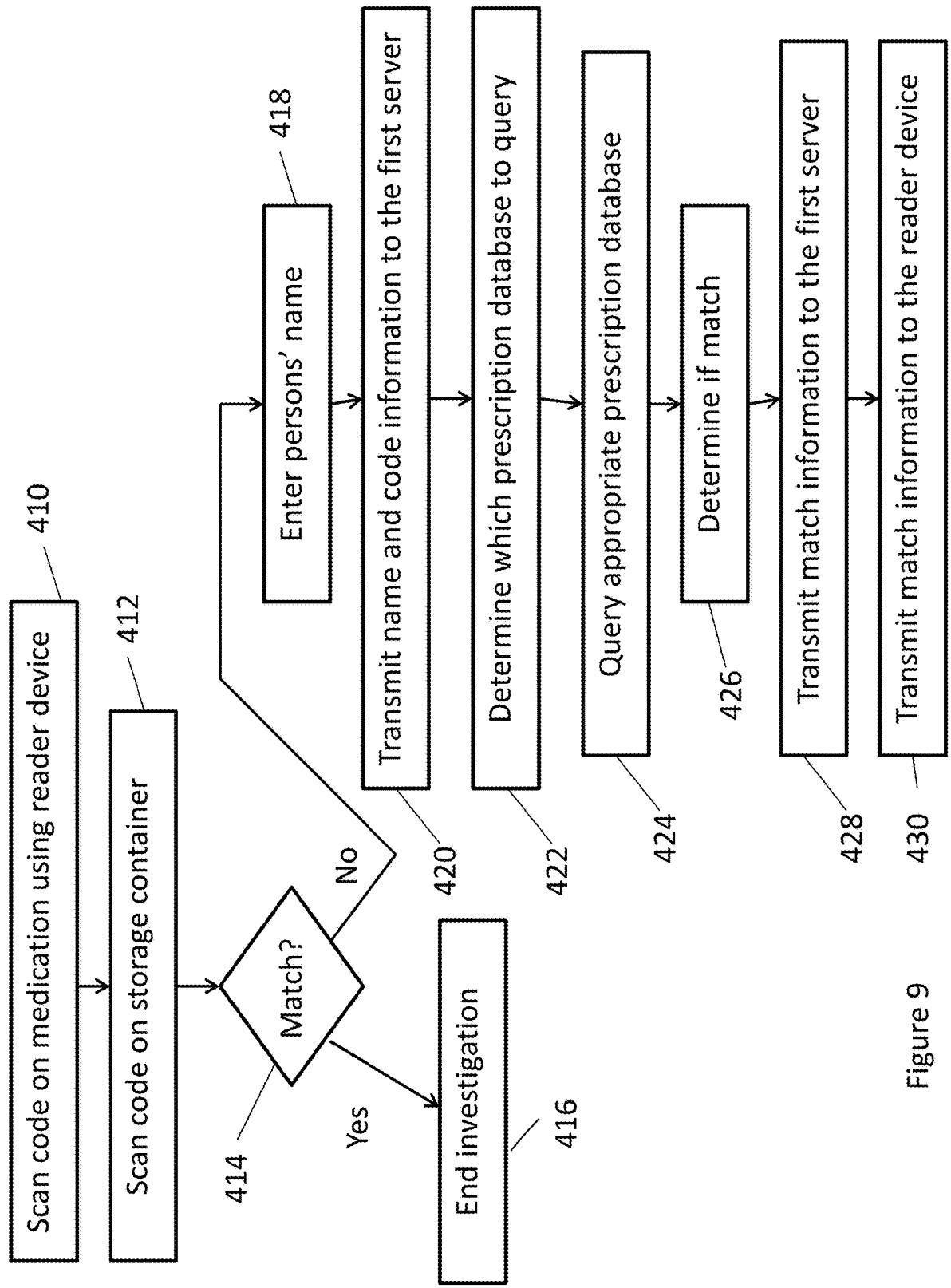
FIG. 9 is another exemplary method.

FIG. 9 illustrates another method whereby in step 410 the code 24 on the medication 12 may be scanned using the reader device 16. In step 412 the corresponding code 26 on the storage container 14 may likewise be scanned by the reader device 16. At step 414 it may be determined if there is a match by any of the several methods previously discussed. If there is a match, as noted in step 416 the investigation may be ended. If there is no match, the same procedure may be followed for steps 418, 420, 422, 424, 426, 428, and 430, which generally corresponds to steps 312, 314, 316, 318, 320, 322, and 324 of FIG. 8, respectively. It is contemplated that step 418 is optional and may be skipped and a procedure similar to steps 210, 212, 214, 216, 218, and 220 of FIG. 7, respectively, may instead be followed.

Figure 10:
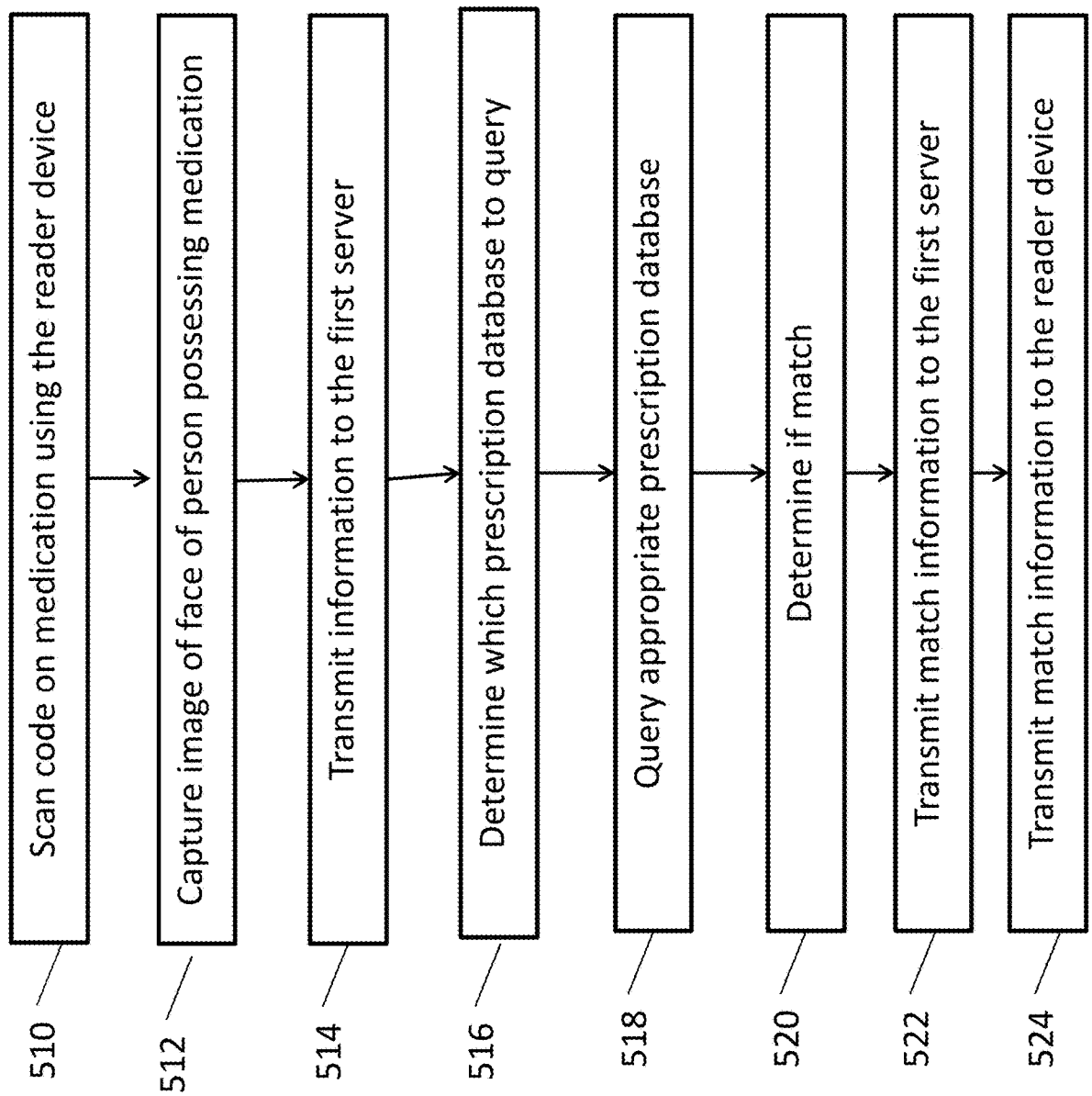
FIG. 10 is another exemplary method in accordance with the present invention.

FIG. 10 illustrates another exemplary method whereby facial recognition technology is utilized. The code 24 on the medication 12 may be scanned using the reader device 16 at step 510. Alternatively, or in addition, the code 26 on the storage container 14 may be scanned. Regardless, the scan of the code 24 or code 26 may permit the reader device 16 to extract an embedded serial number. At step 512 an image of the face of the person in possession of the medication 12 may be taken. The image may be captured using the reader device 16. In such embodiments, the reader device 16 may comprise one or more cameras capable of photographing an individual's face.

In exemplary embodiments, initial facial recognition processing, such as but not limiting to, extracting facial characteristic data from the image of the captured face (e.g., eye spacing distance, distance from forehead to chin, etc.) may be performed at the reader device 16 such that the extracted facial characteristic data is transmitted. In other exemplary embodiments, such initial facial recognition processing may be performed at the prescription database 22 and simply the image data may be transmitted. In still other exemplary embodiments, the initial facial recognition processing may be performed at the first server 18. Regardless, at step 514 the extracted serial number as well as the facial characteristic data or the image data may be transmitted to the first server 18. The first server 18 may determine which prescription database 22 to query at step 516.

One or more entries on one or more of the prescription databases 22 may comprise facial characteristic data for persons prescribed medications 12. The facial characteristic data may be extracted from an image of the person prescribed the medication. Such images may be captured at the dispensing, prescribing, or the like of such medications 12. The image processing required to extract the facial characteristic data may be performed where the image was captured, at the first server 18, or at the prescription database 22.

Regardless, at step 518 the appropriate prescription database 22 may be queried. The query may return the facial characteristic data associated with the queried serial number. At step 520 a match between the facial characteristic data of the person possessing the medication and the retrieved facial characteristic data associated with the queried serial number may be determined. At step 522 the match information may be transmitted to the first server 18. The match information may indicate a match or no match between the facial characteristic data of the person possessing the medication and the retrieved facial characteristic data associated with the queried serial number.

At step 524 the match information may be transmitted to the reader device 16 for display. The reader device 16 may be configured to simply display whether or not a match was received. For example, without limitation, the words "match" or "no match" may be displayed. The results may be color coded for ease of review, such as green for match and red for no match.

In still other exemplary embodiments, the facial characteristic data for the person prescribed the medication may be transmitted to the reader device 16 which performs the match analysis. If no facial characteristic data is available for the individual, other methods and systems may be utilized such as but not limited to, those shown and described herein.

The components described herein, such as but not limited to, the reader device 16, the first server 18, and the prescription database 22 may each comprise one or more electronic storage devices which comprise executable software instructions and one or more processors for executing said executable software instructions. The execution of said executable software instructions may configure the respective device (i.e., the reader device 16, the first server 18, or the prescription database 22) to perform one or more functions described herein.

The various methods discussed herein are merely exemplary and may be performed in any order. Additionally, various steps may be repeated or omitted.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A system for verifying proper possession of a medication comprising:
   a code printed on the medication comprising an embedded serial number, wherein the medication is a pill, tablet, or capsule, and wherein the code is computer readable;
   a reader device comprising a display and an imaging device, wherein the imaging device is adapted to read the code and extract the embedded serial number and capture an image of a face of a person in possession of the medication, wherein said reader device is further configured to receive location information corresponding to a geographic location;
   a prescription database system comprising a number of prescription databases, wherein each prescription database is associated with a geographic area and comprises a number of serial numbers, wherein each serial number is associated with a prescribed medication, patient identity information for the recipient of the prescribed medication, and facial characteristic data for the recipient of the prescribed medication; and
   a first server in electronic communication with the reader device and the prescription database system comprising a processor, an electronic storage device, and executable software instructions stored on the electronic storage device, which when executed by the processor configure the first server to:
     receive said embedded serial number, image data corresponding to the captured image, and location information from said reader device;
     determine which prescription database in the prescription database system to query by determining which prescription database is associated with a geographic area comprising the geographic location;
     query said prescription database based on the embedded serial number;
     retrieve the facial characteristic data from the prescription database system associated with one of the number of serial numbers matching the queried embedded serial number;

determine if the retrieved facial characteristic data matches facial characteristic data extracted from the captured image; and transmit match information to said reader device indicating whether said retrieved facial characteristic data matches the extracted facial characteristic data, but not transmitting the patient identity information;

wherein said reader device is configured to display said match information;

wherein said first server is remote from said reader device; and wherein said match information comprises an indication of the presence or non-presence of a match such that patient identity information for the recipient of the prescribed medication is not received or displayed.

2. The system of claim 1 further comprising:

a wireless communication device located in said reader device and configured to place said reader device in electronic communication with the first server.

3. The system of claim 1 wherein:

all medications dispensed with a given prescription are marked with the same code.

4. The system of claim 1 further comprising:

a reader device processor;

a reader device electronic storage device; and reader device executable software instructions stored on said reader device electronic storage device, which when executed by the reader device processor configure the reader device to extract the facial characteristic data from the captured image;

wherein the image data comprises the extracted facial characteristic data.

5. The system of claim 1 wherein:

the code is a QR code.

6. The system of claim 1 wherein:

the code is a bar code.

7. A system for verifying proper possession of a medication comprising:

a code printed on the medication comprising an embedded serial number, wherein the medication is a pill, tablet, or capsule, and wherein said code is computer readable and is selected from the group consisting of: a bar code and a QR code;

a smartphone comprising:

an imaging device adapted to read the code and capture an image of a person found in possession of the medication;

a location device adapted to receive location information corresponding to a geographic location;

a processor;

an electronic storage device;

executable software instructions stored on the electronic storage device, which when executed by the processor configure the smartphone to translate said scanned code into said embedded serial number and extract facial characteristic data from said captured image; and a wireless transmitter and receiver configured to transmit said embedded serial number, said extracted facial characteristic data, and said geographic location;

a prescription database system comprising a number of serial numbers, each associated with a prescribed medication and facial characteristic data associated with the recipient of said prescribed medication, wherein said prescription database system comprises a number of databases, each database being associated with a geographic area; and a first server in electronic communication with the smartphone and the prescription database system, wherein said first server comprises executable software instructions stored on a first server electronic storage device, which when executed by a first server processor configure the first server to:

receive said embedded serial number from said smartphone;

receive said extracted facial characteristic data from said smartphone;

receive said geographic location from said smartphone;

query a database in the prescription database system which is associated with a geographic area comprising the geographic location to retrieve receive the facial characteristic data associated with serial number matching the queried embedded serial number; and transmit said associated facial characteristic data to said smartphone;

wherein said smartphone comprises additional executable software instructions stored on the electronic storage device, which when executed by the processor configure the smartphone to determine if said extracted facial characteristic data matches said received facial characteristic data and display a message indicating whether the information is a match without displaying identifying information for said recipient of said medication; and wherein the first server is remote from the smartphone.

8. The system of claim 7 wherein:

the embedded serial number comprises a lot number.

9. The system of claim 7 wherein:

the embedded serial number comprises a batch number.

10. The system of claim 7 wherein:

each database in the prescription database system further comprises associated patient information for each of said serial numbers, wherein said associated patient information comprises the medication type, the amount of medication prescribed, the dispensing date, and the expected duration of the prescription; and said first server comprises additional executable software instructions stored on the first server electronic storage device, which when executed by the first server processor configures the first server to retrieve the associated patient information if no facial characteristic data is stored for said queried serial number.

11. A method for verifying proper possession of a medication comprising the steps of:

printing a code on the medication, wherein said code is computer readable and comprises an embedded serial number, wherein the medication is a pill, tablet, or capsule;

providing a reader device comprising a camera, and a first server remote from the reader device and adapted to relay information to and from said reader device, and a prescription database system comprising a number of databases, each database being associated with a geographic area and comprising a number of serial numbers, each serial number being associated with a prescribed medication and facial characteristic data for the recipient of said prescribed medication;

scanning the code on the medication using the reader device to extract the embedded serial number;

receiving location information corresponding to a geographic location from the reader device;

capturing, by way of the reader device, an image of the face of a person in possession of the medication;

extracting facial characteristic data from the captured image;

transmitting the embedded serial number to the first server;

querying the database in the prescription database system associated with a geographic area comprising the geographic location to retrieve the facial characteristic data associated with the embedded serial number;

determining, at the first server, that the retrieved facial characteristic data matches the extracted facial characteristic data; and displaying an indication that a match was found at the reader device without displaying identifying information for the recipient of said medication.

12. The method of claim 11 wherein:

the extraction of facial characteristic data is performed at the reader device.

13. The method of claim 11 wherein:

the extraction of facial characteristic data is performed at the first server.

14. The method of claim 11 wherein:

the extraction of facial characteristic data is performed at the prescription database system.

15. The method of claim 11 wherein:

the determination of a match is performed at the reader device.

16. The method of claim 11 wherein:

the determination of a match is performed at the prescription database system.

* * * * *